United States Patent [19]

Desai

[11] Patent Number: 5,322,503

[45] Date of Patent: Jun. 21, 1994

[54] ENDOSCOPIC SURGICAL INSTRUMENT

[76] Inventor: Ashvin H. Desai, 2338 Walsh Ave., Santa Clara, Calif. 95051

[21] Appl. No.: 779,108

[22] Filed: Oct. 18, 1991

[51] Int. Cl.$^5$ .............................................. A61M 1/00
[52] U.S. Cl. ........................................ 604/21; 604/33; 604/35; 606/41; 606/49
[58] Field of Search ................. 604/21, 27, 30, 32–34, 604/35, 902, 167, 249; 606/39–41, 45, 46

[56] References Cited

U.S. PATENT DOCUMENTS

| | | | |
|---|---|---|---|
| 1,314,855 | 9/1919 | Carpenter | 604/33 |
| 3,828,780 | 8/1974 | Morrison . | |
| 3,850,175 | 11/1974 | Iglesias | 606/46 |
| 4,668,215 | 5/1987 | Allgood . | |
| 4,673,393 | 6/1987 | Suzuki et al. | 604/167 |
| 4,895,565 | 1/1990 | Hillstead | 604/167 |
| 5,071,419 | 12/1991 | Rydell et al. | 604/35 |
| 5,125,910 | 6/1992 | Freitas | 604/249 |
| 5,186,714 | 2/1993 | Boudreault et al. | 604/35 |
| 5,190,541 | 3/1993 | Abele et al. | 604/35 |
| 5,195,958 | 3/1993 | Phillips | 604/33 |
| 5,197,963 | 3/1993 | Parins | 606/41 |
| 5,219,348 | 6/1993 | Buess et al. | 606/40 |

FOREIGN PATENT DOCUMENTS 327410 8/1989 European Pat. Off. .

Primary Examiner—Ralph Lewis
Attorney, Agent, or Firm—Claude A. S. Hamrick

[57] ABSTRACT

An endoscopic surgical instrument 20 includes an irrigation port 21 and an evacuation port 22. Each port, 21 and 22, is connected through independent valves 23 and 24, respectively to a single access conduit 25. The connection between the valves 23 and 24 and conduit 25 is along connector tubes 23a and 24a. The access conduit 25 leads from the valves and their respective valve conduits to a probe connector 26. This probe connector 26 is designed to receive one end, the locating end 27, of a surgical probe 28 which would be used during microsurgical procedures. The surgical instrument 20 also includes a port 31 which allows the surgeon to insert microsurgical instrumentation (not shown) along the access conduit 25 and the bore of the hollow probe 28 to exit from the end 32 thereof. The port 31 should provide a fluid-tight seal when no microsurgical instrumentation is being used with the surgical instrument 20. This will prevent fluid which may be moving along the access conduit 25 to or from the patient, from leaking.

14 Claims, 4 Drawing Sheets

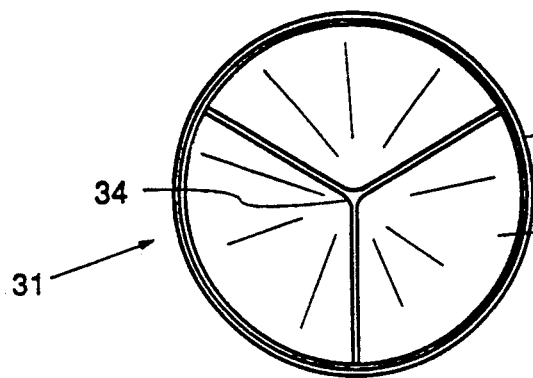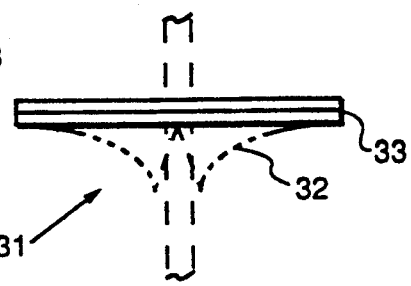
Fig. 3a    Fig. 3b
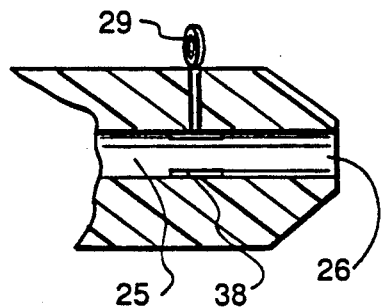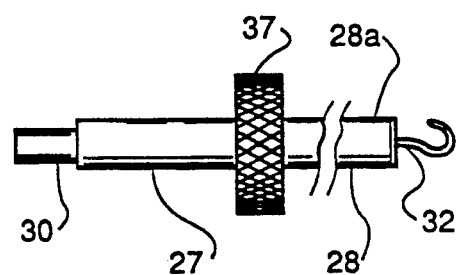
Fig. 4a    Fig. 4b
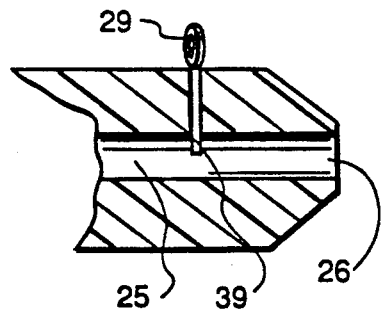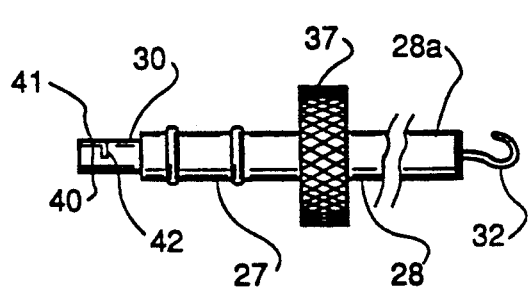
Fig. 5a    Fig. 5b

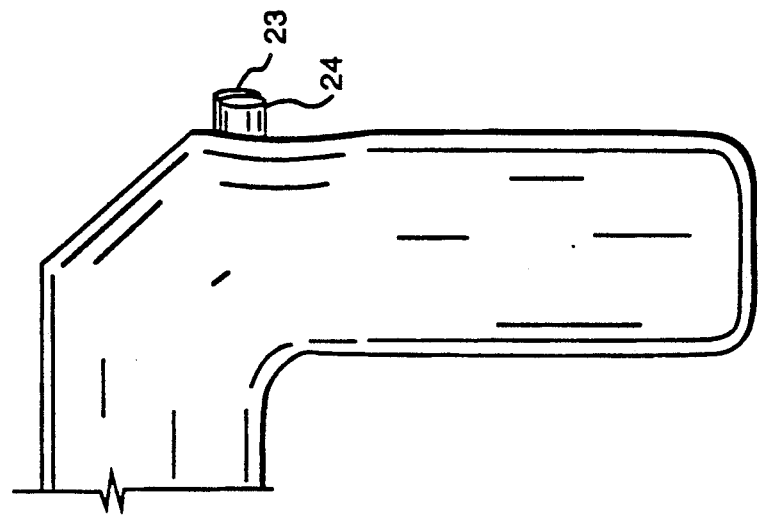
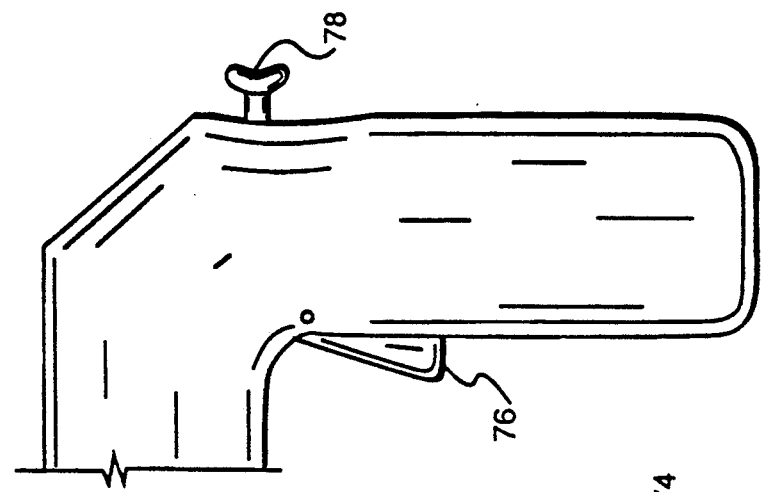
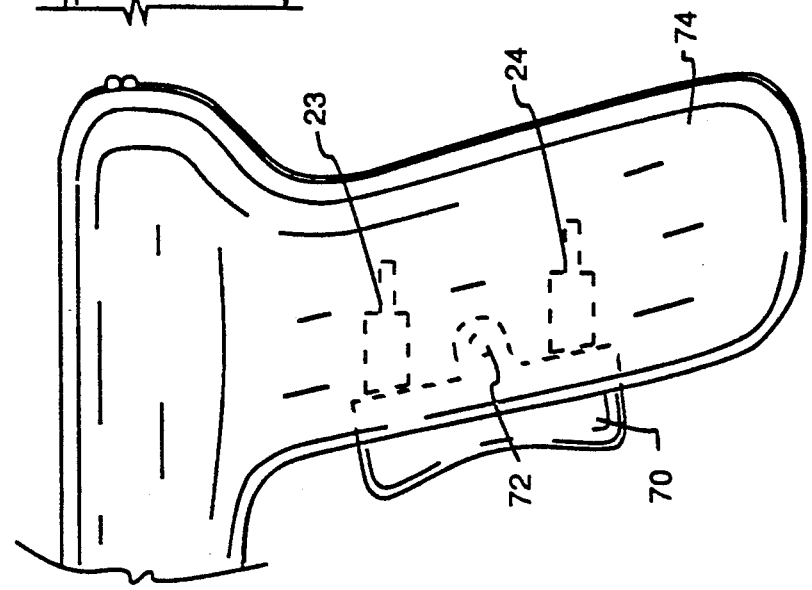

ENDOSCOPIC SURGICAL INSTRUMENT

TECHNICAL FIELD

This invention relates to a surgical instrument and more particularly to an instrument with the capability for automatic irrigation and evacuation of a patient during Laparoscopic or Endoscopic surgical procedures. This invention also relates to irrigation/evacuation control valves for such an instrument.

BACKGROUND ART

Laparoscopic/endoscopic surgical procedure allows a surgeon to see inside the body of a patient without the necessity of large incisions. This reduces the chances of infection and other complications related to large incisions. The laparoscope (or endoscope) further allows the surgeon to manipulate microsurgical instruments within its housing without impeding the surgeon's view of the area under consideration.

During these surgical procedures it is desirable for as few lines as possible to enter the body of the patient. This reduces the size of the incision the surgeon needs to make. It follows from this that the greater the number of functions provided by a single instrument or the greater the number of instruments able to be passed through a single line entering the patient's body, the better.

Furthermore, in certain procedures it may be desirable to irrigate the area under consideration. This in turn necessitates the evacuation of the irrigation fluid or, when bleeding has occurred, the blood or fumes or tissue residue generated by the surgical procedure. From what has been said above it is preferable for both irrigation and evacuation to be conducted along a single conduit which, in turn, acts as an access line for surgical instruments.

A typical device which is used in laparoscopic procedures is an electrosurgical probe. Typically such a probe will comprise an radio frequency energy conductive tube covered with a dielectric material such as polyolefin. At one end, for convenience called the operational end, each probe could have any one of a number of functionally shaped electrodes. In addition a probe could have its end formed specifically for irrigation and/or evacuation.

As the electrodes at the end of the probe are not necessarily symmetrical about the longitudinal axis of the probe, it is desirable for the probe to be mounted on its supporting instrument to permit rotation thereof about this axis. This would allow the manipulation of the operational end of the probe without unnecessary and inconvenient manipulation of the surgeon's arm. In addition, as a variety of electrode shapes are available to the surgeon it is desirable for these probes to be interchangeable.

Furthermore, any valves controlling the evacuation and irrigation procedures should be constructed so as to minimize the possibility of the valve malfunctions if, for example, any tissue or blood coagulates around their moving parts. Similarly if any of the instrumentation is to be reusable, such instrumentation, including the valves, should be capable of being efficiently cleaned by, for example, flushing.

U.S. Pat. No. 4,668,215 (Allgood) discloses a valve for switching between an evacuation and an irrigation conduit and allowing both such evacuation and irrigation to be done via a single line entering the patient. The mechanism for switching between the irrigation, evacuation and closed configurations is by means of a L-valve or T-valve. This patent, in another embodiment thereof, further provides for a piston valve for making an on-off connection between an evacuation port and the line leading into the patient.

The L- and T-valves have the disadvantage that they must be manipulated by rotation by the surgeon, usually using his/her free hand. The piston valve disclosed in this patent has the disadvantage that it has many areas where blood and tissue accumulation and coagulation can occur which may result in the malfunctioning of the valve. In addition, the piston valve has numerous "dead" areas where fluid flow would not occur. This precludes the device from being effectively cleaned by commonly used flushing techniques. Finally, the Allgood patent does not disclose a single body for housing an evacuation/irrigation control valve together with a housing for laparoscopic and microsurgical instrumentation.

A surgical valve that the applicant is aware of is the piston valve illustrated in FIG. 1 of the accompanying drawings.

In this valve a piston 10 is located within a cylinder 11. The piston 10 can be moved along the bore of the cylinder 11 by means of a plunger 12, from a closed position (as shown) to an open position in which a conduit 13 is aligned with an access port 14. This allows fluid flow along a path to or from access port 14, via conduit 13 and space 16 from or to a further port 15. Upon release of the plunger 12 the piston 10 returns to its closed position under action of a spring 17.

This valve, although easy to use, has the disadvantage that blood and tissue accumulation occurs in space 16 and clogs both the space and the spring 17. This may result in undesirable over-evacuation or irrigation of the patient during surgical procedures.

OBJECT OF THE INVENTION

It is therefore an object of this invention to provide a surgical instrument which includes control means to allow for the irrigation and evacuation of a patient during microsurgical procedures, with both irrigation and evacuation being performed along a single line into the patient. The instrument should also act as a mounting for electrosurgical probes and microsurgical instruments.

A further objective of the invention is to provide a mounting for electrosurgical probes which allows for the interchanging of probes as well as allowing a probe mounted on the instrument to be rotated about its longitudinal axis.

Yet another object of the invention is to provide a configuration for an instrument which, depending on the material it is constructed of, can be both disposable and non-disposable. In the event that the instrument is non-disposable it is an object of the invention to provide the instrument with conduits, access ports and valves which can easily be cleaned by means of commonly used flushing techniques.

Finally it is an object of this invention to provide an instrument which can be controlled using only one hand of the user.

SUMMARY OF THE INVENTION

According to this invention, an endoscopic surgical instrument comprises an irrigation and an evacuation port, each port being connected through independent valves to a single access conduit; a probe connector located at one end of the access conduit, the probe connector being for receiving and retaining a hollow surgical probe; and a radio frequency connector which exits into the access conduit in such a manner so as to make radio frequency connection with a probe received by the probe connector.

Preferably the instrument includes a port which opens to allow the ingress of microsurgical instrumentation into the access conduit and along the bore of a hollow probe received by the probe connector.

The port for allowing ingress of the microsurgical instruments should provide a fluid-tight seal when no microsurgical instruments are passed through it. Typically, the ingress port could be in the form of a commercially available tricuspid valve.

Preferably the connector for receiving an end, for convenience called the locating end, of the probe would be in the form of a receiving bore in the access conduit which would include a plurality of O-rings which provide a fluid-tight seal around the locating end of the probe. These O-rings also function to retain the probe in the receiving port while allowing the probe to be rotated. In one embodiment of the invention, the O-rings are, instead of being located within the receiving bore of the access conduit, located about the locating end of the probe.

The radio frequency connector could typically be in the form of a banana connector located on any convenient portion of the body of the surgical instrument.

The radio frequency connector can exit into the receiving bore by means of radio frequency energy conductive plates which make radio frequency connection with a complemental formation on a suitably designed locating end of the probe.

Alternatively, the radio frequency connector exits into the receiving bore or into the access conduit in the form of an intrusive pin which, when a probe is located in the bore, engages a complemental slot in the locating end of the probe. The slot in question would be L-shaped such that when the locating end of the probe is inserted in the receiving bore of the access conduit with the pin located in the axially orientated leg of the L-shaped formation, the rotation of the probe about its longitudinal axis would cause the pin and the axially transverse leg of the L-shaped formation to engage each other thus locking the probe into position. This operation is very much the same as that of the bayonet-type of connector found on certain motor vehicle light bulbs. In this embodiment of the invention, the probe cannot be rotated through the full 360° as with other embodiments.

This invention also provides for a valve, for use as either an evacuation or an irrigation valve, the valve comprising a housing, an activator connected to the housing, at least a first and a second valve access conduit, both of which exit into the housing and a fluid impervious seal mounted within the housing such that activation of the activator causes the first valve conduit to move axially relative to the seal and the second valve conduit such that the seal is disengaged and the conduits are placed in direct fluid communication with each other.

More particularly, the valve comprises a hollow tube in which a spring and the second valve conduit is located. Between the spring and that conduit a seal is located. The other conduit is mounted on the tube and opens into the interior thereof through a hole in the wall of the tube. In the valve's closed position the seal seals the hole in the wall of the tube and prevents fluid communication between the two valve conduits. When the tube is moved axially towards the second valve conduit and against the bias of the spring, the seal is moved away from covering the hole in the tube wall and the valve conduits are placed in communication with each other. This allows the transmission of a fluid or a vacuum between these two conduits.

More specifically, the tube would be located on the longitudinal axis of the second access conduit. The first valve conduit would be mounted on the side wall of the tube such that when the tube moves axially towards the second conduit, the seal bears against one end of the second valve conduit which in turn pushes the seal along its axial line against the bias of the spring and at the same time brings the hole in the wall of the tube into direct alignment with a complemental hole in the second valve conduit. This allows fluid flow directly between the two conduits with a minimum of space between the respective ends of the two conduits. For this to be effectively achieved, the second conduit should be a snug fit within the inner bore of the tube.

For ease of use the tube can be closed at one end to form a button.

Typically, the instrument of the invention would contain two such button operated valves. One valve would act as an evacuator control while the other valve would act as an irrigation control. Both valves communicate into a single access conduit which, when the instrument is in use, leads into the patient via the receiving bore and the hollow interior of the electrostatic probe.

Typically the endoscopic surgical instrument of the invention would be in the form of a pistol with the "barrel" portion thereof having, at one end thereof, the receiving bore for the locating end of the endoscopic probe and, at the other end thereof, the access port for the microsurgical instruments.

The valves for controlling the evacuation and irrigation procedures may be mounted in the "handle" portion of the pistol-shaped instrument. The valves may be mounted alongside one another in the handle portion and may protrude therefrom to allow finger control by the surgeon using the instrument.

The valves may also be operated by a rocker-shaped "trigger" pivotally mounted between the two valves. A trigger of this nature would, on activation by the surgeon's fingers, be pivotable from a position where it activates the evacuation valve, through a closed, inactive position, to a position where it activates the irrigation valve. Irrigation and evacuation cannot, with a trigger of this nature, be activated simultaneously.

Alternatively, the evacuation and irrigation valves may be mounted at the top end of the pistol handle and towards the back thereof to allow the surgeon to operate the evacuation/irrigation procedure with his/her thumb. The activation buttons for the valves would typically be differently shaped so that the surgeon could determine the function of the buttons by feel only.

Alternatively a combination of a trigger mechanism, for evacuation and a button for irrigation, say, could be used.

Various embodiments of the invention will now be further illustrated with reference to the following drawings.

DESCRIPTION OF THE DRAWINGS

In the following drawings:

FIGS. 3a and 3b are an illustration of a tricuspid valved access port illustrated in plan (a) and elevation (b) views;

FIGS. 4a and 4b are sections through a receiving bore and locating end of the instrument according to one embodiment of the invention;

FIGS. 5a and 5b are sections through a similar receiving bore and locating end showing a further embodiment of the invention;

FIGS. 9, 10 and 11 are diagrammatic illustrations showing various configurations of valve operating buttons and triggers.

DETAILED DESCRIPTION OF EMBODIMENTS OF THE INVENTION

Figure 1:
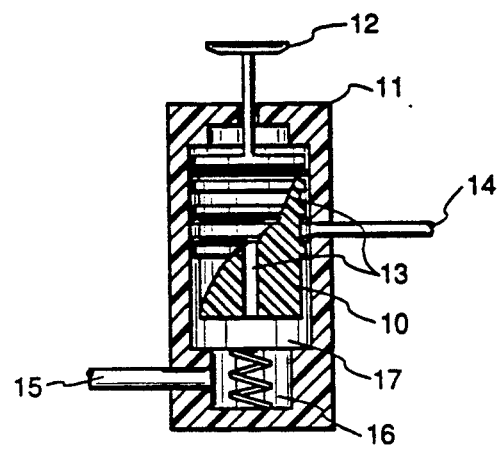
FIG. 1 is a partial sectional elevation through a prior art piston valve.
Figure 2:
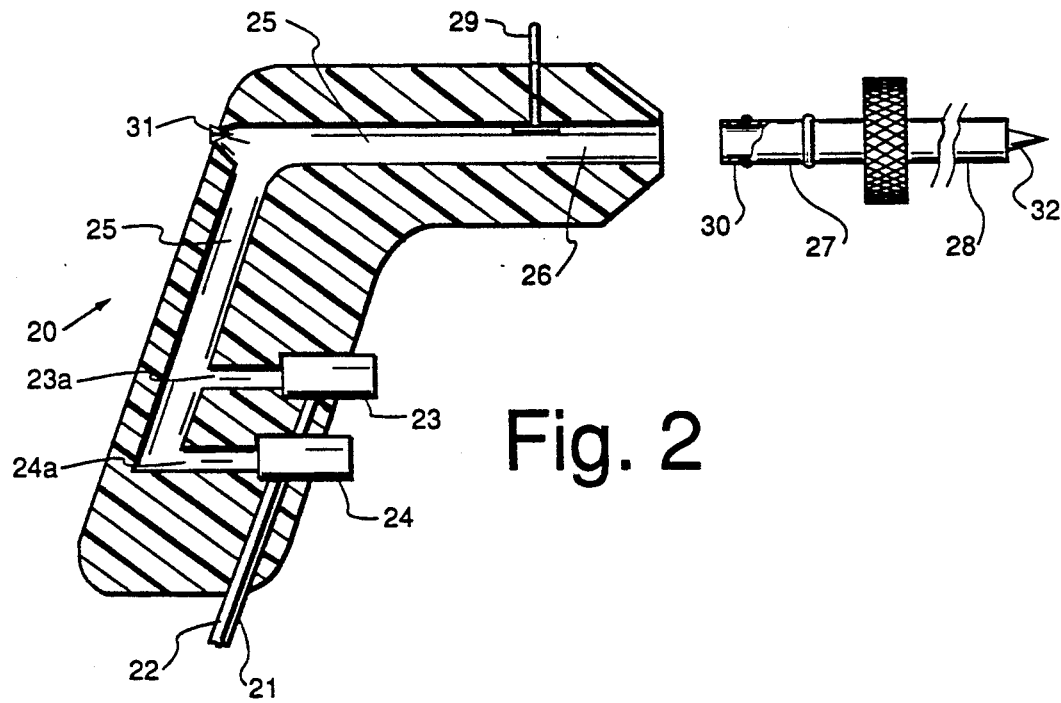
FIG. 2 is a diagrammatic section through a semi-exploded elevation of the endoscopic surgical instrument of the invention.

In FIG. 2 of the accompanying drawings, the endoscopic surgical instrument of the invention is generally indicated as 20. The instrument 20 is shown to include an irrigation port 21 and an evacuation port 22. Each port, 21 and 22, is connected through independent valves 23 and 24, respectively to a single access conduit 25. The connection between the valves 23 and 24 and conduit 25 is along connector tubes 23a and 24a.

The access conduit 25 leads from the valves and their respective valve conduits to a probe connector 26. This probe connector 26 is designed to receive one end, the locating end 27, of a surgical probe 28 which would be used during microsurgical procedures. The connection 26 is described in more detail with reference to FIGS. 4 and 5 hereafter.

At or near the probe connector 26, a radio frequency connector 29 is located. As illustrated, this is in the form of a banana connector. The advantage of a banana connector is that it is an industry standard and can be used for connecting the instrument 20 to regular frequency supply sources manufactured by a number of different manufacturers.

The radio frequency connector 29 exits into the access conduit 25 where it makes connection with a point 30, on the locating end 27 of a probe 28 received by the probe connector 26.

The surgical instrument 20 also includes a port 31 which allows the surgeon to insert microsurgical instrumentation (not shown) along the access conduit 25 and the bore of the hollow probe 28 to exit from the end 32 thereof. The port 31 should provide a fluid-tight seal when no microsurgical instrumentation is being used with the surgical instrument 20. This will prevent fluid which may be moving along the access conduit 25 to or from the patient, from leaking.

Typically, the access port 31 would be in the form of a commercially available tricuspid valve as illustrated in FIGS. 3(a) and (b). In these Figures, the valve 31 is shown as being constituted by three segments 32 which in plan view are wedge-shaped and which together form the disc shaped sealing portion of the valve. The segments 32 are held together by means of a circumferencial ring 33 which biases the three segments 32 together to form a fluid impervious seal. In use, the microsurgical instrumentation would be inserted through the valve at a point 34 where the apexes of the segments 32 come together. This insertion would force the elements of the valve apart to allow ingress of the microsurgical instrumentation. The effect thereof is shown in broken lines in FIG. 3(a). When the instrumentation is removed from the valve 31, the segments 32 are pulled together to form the seal.

In FIGS. 4a and 4b, the probe connector 26 is shown to be constituted by a receiving bore which is coaxial with the fluid access conduit 25. In practice, the diameter of this bore would be the same as that of the access conduit 25 and would be sized to receive the locating end 27 of the probe 28 in a relatively close fit. Within the bore forming the probe connector, a plurality, typically two, O-rings 36 are located. When the locating end 27 is inserted into the bore 26 these O-rings provide a snug, fluid-tight seal about the end 27. Once the locating end 27 of the probe is received within the bore 26 it is capable of being rotated about its longitudinal axis, by means of a knurled rotation knob 37 located between the locating end 27 and the operational end 32 of the probe 28.

The probe 28 would typically be made of a electrostatic conductive material coated with a non-conductive material such as heat shrink polyolefin. Electrostatic/radio frequency energy is passed along the probe 28 from the radio frequency connector 29 via electrostatically conductive plates 38 located within the bore of the probe connector 26 and onto the end 30 of the probe 28. The end 30 is so designed such that when the locating end 27 of the probe is received by the probe connector 26, electrostatic connection is made between the plate 38 and the connector 30. This allows the surgeon to pass energy into the patient being operated on.

An alternative radio frequency connector is illustrated in FIGS. 5a 5b. In this case, the banana connector 29 exits into the bore 26 in the form of a pin 39. In the conductive end 30 of the probe 28 an L-shaped slot 40 is formed. As the probe 28 is inserted into the receiving bore 26, the pin 39 engages the axially-orientated leg 41 of the L-shaped slot 40. When the probe can be inserted no further along the bore it is twisted, in this case in an anti-clockwise direction, such that the pin 39 and the axially transverse leg 42 of the L-shaped slot 40 engage each other to lock the probe 28 into position. In this embodiment the probe 28 cannot be rotated by means of the knurled knob 37.

FIG. 5 further illustrates an alternative positioning of the O-rings 36. In this case they are located on the locating end 27 of the probe 28.

From FIGS. 4 and 5, although not shown, it will be apparent that the diameter of the operational shank 28a of the probe 28 can be variable. Typically, the probe, as shown, would have a diameter of 5 mm. This diameter can, however, be increased to 10 mm which would be close to the diameter of the locating end 27 of the probe, as well as that of the internal bore diameter of the access conduit 25. The advantage of 10 mm diameter probes is that the evacuation of removed tissue and objects such as the gall-stones can be more effectively achieved. Obviously, when the bore of the operating shank 28a of the probe, the locating end 27 and the access conduit 25 are all 10 mm in diameter, the diameter of the evacuation port 22 and its related valve 24 and connector tube 24a must also be 10 mm.

In FIGS. 6(a) to (i), a number of different electrode shapes are illustrated. These electrode tips would be located on the operating end of the probe 28.

As can be seen from the Figure, a number of the tips are not symmetrical about the longitudinal access of the probe 28. It is for this reason that it is desirable for the probe 28 to be mounted on the instrument in such a manner to allow for a rotation of the probe about its longitudinal axis. As has been previously indicated, this will give the surgeon the opportunity of rotating any non-symmetrical tips, inside the patient, without having to rotate his or her wrist.

Figure 6:
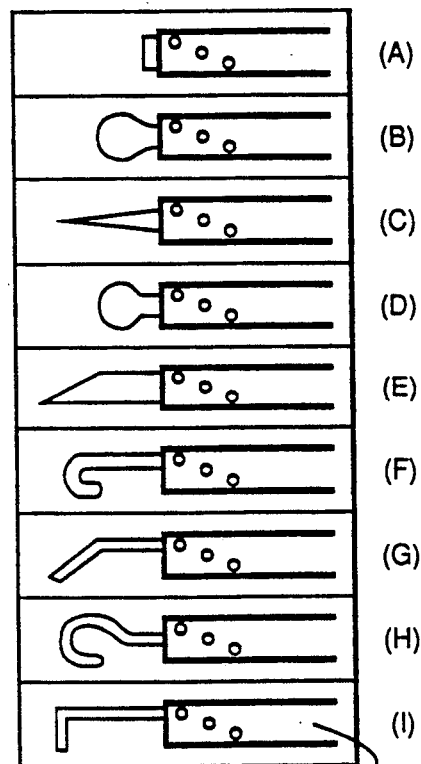
FIGS. 6(a)-(i) illustrates various electrostatic probe operational ends.

This invention extends also to an electrostatic probe 28, substantially as described in any of the FIGS. 4 to 6.

Figure 7:
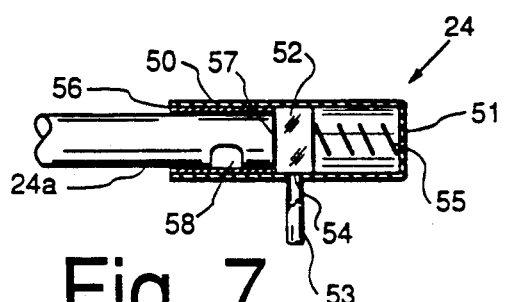
FIG. 7 is a section through a valve according to the invention with the valve being in the shut position.
Figure 8:
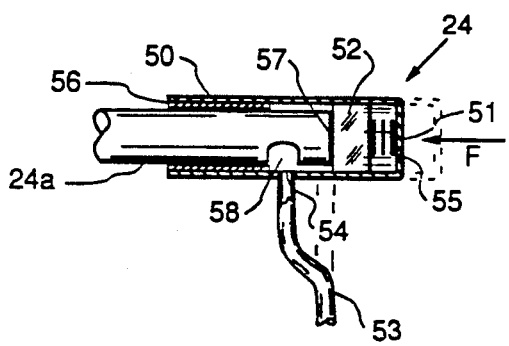
FIG. 8 is the valve of FIG. 7 in the open position.

The details of the irrigation/evacuation valve are illustrated in FIGS. 7 and 8. The valve 24 indicated in both Figures comprises a housing constituted by a hollow tube 50 and an activator in the form of a button 51 formed integrally with the tube 50. A fluid impervious seal 52 is located within the tube 50. Referring specifically to FIG. 7, in which the valve is shown in the shut position, it can be seen that the seal 52 lies between a first valve conduit 53 which leads to the evacuation port 22 (not shown) and a second valve conduit in the form of connector tube 24a which leads into the primary access conduit 25 of the surgical instrument. In effect, the seal 52 prevents the conduits 53 and 24a from being in communication with each other.

The first valve conduit 53 is mounted onto the wall of the tube 50 and opens into the interior of the tube 50 through a hole 54. Between the seal 52 and the button portion 51 of a tube 50, a spring 55 is located. On the side of the seal 52, opposite to which the spring is located, a tubular insert 56 is located. This tubular insert has a snug but slidable fit over the outer wall of the second valve conduit 24a as well as a tight, fluid impervious fit into the inner bore of the tube 50. This tube 56 acts as a stop which prevents the spring 55 from pushing the seal 52 out of the hollow tube 50.

To open the valve, as is illustrated in FIG. 8, an activating force, applied along a line F to the button 51, will cause the button to move from the position indicated in broken lines to the illustrated open-valve position. As the button moves, so does the hollow tube 50, taking the first valve conduit 53 along with it. In addition, the leading edge 57 of the second valve conduit 24a bears against the seal 52 causing the seal to move relatively to the tube 50. This in turn disengages the seal from sealing the hole 54 in the wall of the tube 50. The movement of the first valve conduit 53, relative to the second valve conduit 24a, places the respective openings 54 and 58 of these two conduits in fluid communication with each other thereby allowing an unobstructed fluid flow along both access conduits.

Upon release of the force on the button 51, the bias of the spring 55 will return the valve to its shut position.

It is evident from the construction of these valves that they can be readily cleaned by commonly used cleaning techniques such as flushing. In addition, the valves have almost no areas where blood and tissue accumulation and coagulation can occur, and if such accumulation and coagulation does occur the valves cannot be jammed in the open position. This is because the spring biasing the valve into its closed position is located in an effectively sealed area. Furthermore these valves have been tested to a pressure of up to 100 psi without the integrity of the valve seal being adversely affected.

It is preferable that two valves of the above described type will be used on the instrument 10. One valve would act as an evacuation valve while the other as an irrigation valve. The buttons 51 operating these valves could protrude, in a pistol shaped instrument, from the handle thereof to allow manipulation of the valves by means of the surgeons fingers grasped about the handle.

These buttons could also be manipulated by means of a rocker-shaped trigger 70 illustrated in FIG. 9. The trigger 70 is pivotally mounted on a point 72 on the handle 74 of the pistol. Depressing the trigger 70 to operate the irrigation valve 23 would not interfere with the operation of the evacuation valve 24. Similarly, operation of the trigger 70 to operate the evacuation valve 24 would in no way effect the operation of the irrigation valve. It is evident from this Figure that it would be impossible to operate both the irrigation and the evacuation valve simultaneously thus preventing wasteful and undesirable simultaneous evacuation and irrigation.

In FIG. 10 a trigger mechanism 76 is shown for operation of only one of the buttons. The other button 78 would be located for operation by means of the surgeon's thumb in a position removed from the trigger 76. This could, for example, be near the top end of the handle portion of the instrument.

Yet a further positioning of the buttons 23 and 24 is indicated in FIG. 11. In this instance, the buttons protrude from the top rear of the pistol handle and are located side-by-side. To prevent confusion between evacuation and irrigation procedures, the tops of the buttons have different shapes. So, for example, the button to manipulate the evacuation valve could be concave while the button for manipulating the irrigation valve could be convexly shaped.

Finally, it will be apparent to anyone skilled in the art, that the surgical instrument of this invention could be made from any suitable material. In the event that the instrument is intended for use only once, some form of plastic material could be used. Alternatively, for repetitive use of the instrument, the instrument can be made of a more durable material such as aluminum.

I claim:

1. An endoscopic surgical instrument comprising a handle forming housing; an irrigation port and an evacuation port formed in the housing, each port being connected through independent valves to a single access conduit, the conduit being internal to the housing and having a distal end and a proximal end, and each of said ports being connected to the proximal end; a probe connector located at the distal end of the access conduit, the probe connector being in the form of a bore for receiving and retaining a removable hollow surgical probe; a radio frequency connector located on the housing of the instrument and passing through the housing and into the access conduit, said connector being in the form of an intrusive pin which, when an end of the probe is located in the bore, engages a complemental slot in the end of the probe so as to make electrostatic connection with the probe; an aperture formed in the housing and connected to the access conduit; and a closure for the aperture which may be opened to allow the ingress of a microsurgical instrument into the access conduit and along the bore of the hollow probe received by the probe connector, said closure being in the form of a tricuspid valve and providing a fluid-tight seal when no microsurgical instrument is passed through it.

2. An endoscopic surgical instrument as recited in claim 1, wherein the probe connector includes a plurality of O-rings for providing a fluid-tight seal around said end of the probe.

3. An endoscopic surgical instrument as recited in claim 1 in combination with a probe having a plurality of O-rings disposed about an end of the probe, to form a seal between the probe and said bore.

4. An endoscopic surgical instrument as recited in claim 1 wherein said intrusive pin has attached thereto electrostatically conductive plates for making electrostatic connection with a complemental formation on a suitably designed locating end of the probe.

5. An endoscopic surgical instrument as recited in 1 in combination with a probe, having an L-shaped slot such that when an end of the probe is inserted in the receiving bore of the access conduit with the pin located in the axially orientated leg of the L-shaped slot, the rotation of the probe about its longitudinal axis causes the pin and the transverse leg of the L-shaped slot to engage each other thus locking the probe into position.

6. An endoscopic surgical instrument as recited in claim 1, wherein said independent valves include an evacuator control valve and an irrigation control valve both of which communicate with the single access conduit, and wherein each valve comprises a valve housing, an activator connected to the valve housing, at least a first valve conduit and a second valve conduit each having a proximal and a distal end, and the proximal ends of each valve conduit communicating with the valve housing, the distal end of the first valve conduit being in fluid communication with the single access conduit, and the distal end of the second valve conduit being in fluid communication with one of said irrigation port and said evacuation port, a fluid impervious seal disposed in a first position within the valve housing for blocking communication between said first valve conduit and said second valve conduit and such that activation of the activator causes the valve housing and the first valve conduit to move axially relative to the seal and the second valve conduit such that the seal is moved to a second position within the valve housing and the proximal ends of each of the valve conduits are placed in direct fluid communication with each other.

7. An endoscopic surgical instrument as recited in claim 6 wherein the valve housing of each valve is a hollow tube having an open end and a closed end, said valve housing has a spring disposed therein, and wherein the proximal end of the second valve conduit opens into the interior of the tube through a first hole in a wall of the tube with the seal being located between the spring and the first valve conduit, and the first valve conduit being slidably disposed within the open end of the tube and having a second hole in a wall thereof, and the seal being in contact with the spring and the proximal end of the first valve conduit such that in the valve's closed condition the seal covers the first hole in the wall of the tube and prevents fluid communication between the two valve conduits, and such that when the tube is moved axially against the bias of the spring, the seal is moved away from covering the first hole in the tube wall and the first hole and the second hole are aligned, whereby the first valve conduit and the second valve conduits are placed in fluid communication with each other.

8. An endoscopic surgical instrument as recited in claim 7 wherein said handle forming housing is in the form of a pistol which includes a handle grip portion and a barrel portion, the barrel portion having, at one end thereof, the probe connector and, at the other end thereof, the aperture for the microsurgical instrument.

9. The instrument of claim 8 in which the valves for controlling the evacuation and irrigation procedures are mounted in the handle portion of the instrument and wherein the valves are mounted to allow finger control by the surgeon using the instrument.

10. The instrument of claim 9 wherein the valves are operable by a rocker-shaped trigger pivotally mounted between the two valves and which would, on activation by the surgeon's fingers, be pivotable from a position where it activates the evacuation valve, through an inactive position, to a position where it activates the irrigation valve such that irrigation and evacuation cannot be activated simultaneously.

11. The instrument of claim 10 wherein the evacuation and irrigation valves are mounted at the top end of the pistol handle and towards the back thereof to allow the surgeon to operate the evacuation/irrigation procedure with his/her thumb.

12. The instrument of claim 11 wherein the tactile portions of the activation buttons for the valves are differently shaped to allow the surgeon to determine the function of the buttons by feel only.

13. The instrument of claim 8 wherein one valve is operated by a trigger mechanism and the other by means of a button.

14. An endoscopic surgical instrument as recited in claim 6 wherein the activators of said evacuator control valve and said irrigation control valve have tactile portions which are differently shaped to allow a surgeon to determine the function of the associated valve by feel only.

* * * * *